United States Patent [19]
Malamet et al.

US005300700A

[11] Patent Number: 5,300,700
[45] Date of Patent: Apr. 5, 1994

[54] PROCESS FOR THE PRODUCTION OF HIGH-PURITY BISPHENOL A

[75] Inventors: Georg Malamet; Hans-Peter Wirges; Claus Wulff, all of Krefeld; Alfred Eitel, Dormagen, all of Fed. Rep. of Germany

[73] Assignee: Bayer Aktiengesellschaft, Leverkusen, Fed. Rep. of Germany

[21] Appl. No.: 48,219

[22] Filed: Apr. 20, 1993

[30] Foreign Application Priority Data

Apr. 28, 1992 [DE] Fed. Rep. of Germany ....... 4213872

[51] Int. Cl.$^5$ .................... C07C 37/84; C07C 39/16
[52] U.S. Cl. ................... 568/724; 568/722; 568/727
[58] Field of Search ............. 568/727, 724, 722, 723, 568/728

[56] References Cited

U.S. PATENT DOCUMENTS

| 4,354,046 | 10/1982 | Ladewig et al. | 568/724 |
| 4,408,087 | 10/1983 | Li | 568/724 |
| 4,487,979 | 12/1984 | Gaughan | 568/816 |
| 4,529,823 | 7/1985 | Mendiratta | 568/724 |
| 4,954,661 | 9/1990 | Iimuro et al. | 568/724 |
| 5,198,591 | 3/1993 | Kiedik et al. | 568/722 |

FOREIGN PATENT DOCUMENTS

| 0112615 | 7/1984 | European Pat. Off. . | |
| 0330146 | 8/1989 | European Pat. Off. | 568/724 |
| 0475893 | 3/1992 | European Pat. Off. . | |
| 0496898 | 8/1992 | European Pat. Off. | 568/724 |

Primary Examiner—Werren B. Lone
Attorney, Agent, or Firm—Connolly & Hutz

[57] ABSTRACT

The invention relates to a special process for the production of high-purity bisphenol A from acetone and phenol in the presence of acidic catalysts.

8 Claims, No Drawings

PROCESS FOR THE PRODUCTION OF HIGH-PURITY BISPHENOL A

This invention relates to a special process for the production of high-purity bisphenol A from acetone and phenol in the presence of acidic catalysts.

Processes for the production of high-purity bisphenol A from phenol and acetone in the presence of acidic catalysts are known. For example, the excess phenol may be distilled off and the remaining crude bisphenol can be purified by recrystallization from organic solvents, such as toluene. The bisphenol A/phenol adduct can also be crystallized from the reaction mixture, the phenol present therein may be removed by distillation and the remaining bisphenol may be recrystallized as described above. These processes have the disadvantage that external solvents have to be used and worked up.

In addition, it is known that high-purity bisphenol A can be produced by removing most of the phenol from the reaction mixture by distillation and purifying the crude bisphenol thus obtained, i.e. containing less than 10% and preferably less than 3% phenol, by fractional melt crystallization in a dynamic falling-film crystallizer, for example of the type described by Rittner and Steiner in Chem.-Ing.-Techn. 57 (1985), 91 or by Wellinghoff and Wintermantel in Chem.-Ing.-Techn. 63 (1991), 881. This process has the disadvantage that, firstly, a very large quantity of phenol has to be removed by distillation, resulting in high costs and increased and prolonged exposure to heat of the bisphenol A and the secondary products. On the other hand, the crude bisphenol obtained is generally highly impure which necessitates subsequent melt crystallization over many stages until the high purity required is achieved.

A new process for the production of high-purity bisphenol A without any of the disadvantages mentioned above has now been found.

Accordingly, the present invention relates to a process for the production of high-purity bisphenol A—produced in known manner from phenol and acetone in the presence of acidic catalysts—from the reaction solution resulting, characterized in that the reaction solution is cooled until the bisphenol crystallizes in the form of its 1:1 adduct with phenol, this adduct is separated and, at the same time, the phenolic mother liquor removed is returned to the process, phenol is added to the adduct separated in such a quantity that the total phenol content is at least 40% by weight, the resulting mixture is highly purified by fractional melt crystallization and, finally, the adduct obtained is separated by distillation into high-purity bisphenol A (>99% by weight) and phenol which is returned to the process.

The process according to the invention gives bisphenol A in a purity of more than 99.9% by weight. It has the following particular advantages: most of the excess phenol can be removed by filtration, leaving only 1 mol phenol per mol bisphenol to be distilled. In addition, the starting material used in the process according to the invention is highly prepurified material having a p,p-bisphenol content of at least 99.0% by weight so that the number of stages involved in the melt crystallization step is greatly reduced. Finally, the melt crystallization process of the thermolabile material can be carried out at the relatively low melt temperatures of the bisphenol A/phenol adduct (100° to 120° C. as opposed to 160° to 170° C. in the case of phenol-free bisphenol crystallization).

The melt crystallization may be carried out, for example, in a commercially available falling-film crystallizer.

The process according to the invention may optionally be carried out in an inert gas atmosphere (for example nitrogen, noble gases, etc.).

EXAMPLE

A solution of crude bisphenol (p,p-bisphenol containing such secondary products as o,p-bisphenol, indanes, chromanes and trisphenols) is produced in known manner by reaction of acetone with excess phenol on an acidic ion exchanger as catalyst. This reaction solution was cooled to 45° C. in a cooling crystallizer, the 1:1 adduct of already relatively pure p,p-bisphenol and phenol crystallizing. The adduct crystallizing was filtered off and washed with phenol and the filtrate collected was recycled to the reaction The adduct filtered off consisted of 62% by weight bisphenol and 38% by weight phenol (p,p-bisphenol content 99.70% by weight) and contained the following secondary products:

| | |
|---|---|
| o,p-bisphenol | 1390 ppm |
| indanes | 40 ppm |
| chromanes | 300 ppm |
| trisphenol I | 200 ppm |
| trisphenol II | 800 ppm |
| unknown | 270 ppm |

Phenol was added to this adduct in such a quantity that a mixture of 44.2% by weight phenol and 55.8% by weight bisphenol was formed. The mixture was subjected to two-stage melt crystallization in a Sulzer falling-film crystallizer (tube length 12 m, tube diameter 70 mm). This fractional melt crystallization was carried out at a temperature of 100° C. for crystallization, 100° to 120° C. for sweating and 120° to 130° C. for melting of the highly purified adduct.

Finally, the phenol was removed from the highly purified adduct by distillation and returned to the reaction. The highly pure bisphenol obtained had a purity of 99.91% and the secondary products had decreased as follows:

| | |
|---|---|
| o,p-bisphenol | 230 ppm |
| indanes | 0 ppm |
| chromanes | 140 ppm |
| trisphenol I | 50 ppm |
| trisphenol II | 330 ppm |
| unknown | 150 ppm |

What is claimed is:

1. A process for purifying bisphenol A from reaction solutions prepared by reacting phenol with acetone in the presence of acid catalysts, which comprises cooling the reaction solution to crystallize bisphenol into its 1:1 adduct with phenol, separating the adduct from the phenol mother liquor, adding to the separated adduct phenol in such quantity that the total phenol content is at least 40% by weight, purifying the resulting mixture by fractional melt crystallization, and separating the resulting adduct by distillation into bisphenol A and phenol.

2. The process of claim 1 wherein the phenol mother liquor is returned to the process reaction of phenol with acetone.

3. The process of claim 1, wherein the reaction solution is cooled to a temperature of about 45 degrees C.

4. The process of claim 1, wherein the melt crystallization is carried out in an inert gas atmosphere.

5. The process of claim 1, wherein the phenol separated by distillation is returned to the process reaction of phenol with acetone.

6. The process of claim 1, wherein the purified bisphenol A is greater than 99% by weight pure.

7. The process of claim 1, wherein the purified bisphenol A is greater than 99.9% by weight pure.

8. The process of claim 1, wherein melt crystallization is carried out at a temperature of 100 to 120 degrees C.

* * * * *